United States Patent [19]

Poetsch et al.

[11] 4,232,016
[45] Nov. 4, 1980

[54] 3-FLUOROBENZODIAZEPINES

[75] Inventors: Eike Poetsch; Jürgen Uhl; Dieter Marx; Wighard Strehlow; Helmut Müller-Calgan; Giuliano Dolce, all of Darmstadt, Fed. Rep. of Germany

[73] Assignee: Merck Patent Gesellschaft mit beschraenkter Haftung, Darmstadt, Fed. Rep. of Germany

[21] Appl. No.: 639,163

[22] Filed: Dec. 9, 1975

[30] Foreign Application Priority Data

Dec. 20, 1974 [DE] Fed. Rep. of Germany ....... 2460360
Sep. 23, 1975 [DE] Fed. Rep. of Germany ....... 2542251

[51] Int. Cl.³ .................. C07D 243/24; A61K 31/55
[52] U.S. Cl. .................................... 414/244; 424/263; 260/239 BD; 260/239.3 D; 546/328; 546/371; 546/315; 546/316; 546/323; 564/195; 564/211
[58] Field of Search ............... 260/239.3 D; 424/244, 424/263

[56] References Cited

U.S. PATENT DOCUMENTS

| | | | |
|---|---|---|---|
| 3,121,076 | 2/1964 | Keller et al. | 260/239.3 D |
| 3,296,249 | 1/1967 | Bell | 260/239.3 D |
| 3,296,251 | 1/1967 | Bell et al. | 260/239.3 D |
| 3,299,053 | 1/1967 | Archer et al. | 260/239.3 D |
| 3,371,085 | 2/1968 | Reeder et al. | 260/239.3 D |
| 3,429,874 | 2/1969 | Topliss et al. | 260/239.3 D |

OTHER PUBLICATIONS

Sternbach et al., "Some Aspects of Structure–Activity Relationship in Psychotropic Agents of the 1,4-Benzodiazepine Series *CSIR* New Delhi, India (1966).

*Primary Examiner*—Henry R. Jiles
*Assistant Examiner*—Robert T. Bond
*Attorney, Agent, or Firm*—Millen & White

[57] ABSTRACT

3-Fluoro-2,3-dihydro-1H-1,4-benzodiazepin-2-ones of the formula

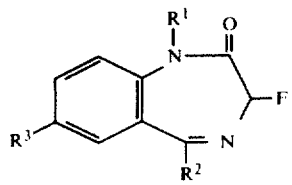

wherein $R^1$ is H, alkyl or fluorinated alkyl of 1-4 carbon atoms and up to 9 fluorine atoms or cycloalkylalkyl of 4-8 carbon atoms; $R^2$ is phenyl; monohalophenyl or pyridyl; $R^3$ is F, Cl, Br or $NO_2$, and physiologically acceptable acid addition salts thereof, are central nervous system depressants.

39 Claims, No Drawings

3-FLUOROBENZODIAZEPINES

BACKGROUND OF THE INVENTION

The invention relates to novel 3-fluoro-2,3-dihydro-1H-1,4-benzodiazepin-2-ones.

Structurally similar compounds which are unsubstituted by a fluorine atom in the 3-position, for example, 1-methyl-5-phenyl-7-chloro-2,3-dihydro-1H-1,4-benzodiazepin-2-one (diazepam) and 3-chlorodiazepam, are known.

SUMMARY OF THE INVENTION

In one composition aspect, this invention relates to 3-fluoro-2,3-dihydro-1H-1,4-benzodiazepin-2-ones of the formula

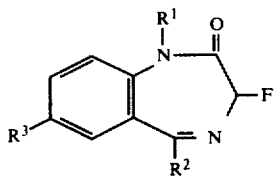

wherein $R^1$ is H, alkyl or fluorinated alkyl of 1–4 carbon atoms and up to 9 fluorine atoms or cycloalkylalkyl of 4–8 carbon atoms; $R^2$ is phenyl, monohalophenyl or pyridyl; $R^3$ is F, Cl, Br or $NO_2$, and physiologically acceptable acid addition salts thereof.

In other composition aspects, this invention relates to intermediates for the production thereof, including those of formulae III, V, VI, VII, VIII, IXa, IXb, IXc, IXd and X, as defined hereinafter.

In a therapeutic aspect, this invention relates to a method for depressing central nervous system activity in mammals by administering to a patient a daily dosage of a 3-fluoro-2,3-dihydro-1H-1,4-benzodiazepin-2-one, of this invention, preferably in admixture with a pharmaceutically acceptable carrier, effective to induce muscle-relaxing, anti-convulsive or anxiolytic effects.

In a further composition aspect, this invention relates to a central nervous system depressant preparation comprising a central nervous depressant amount per unit dosage of a 3-fluoro-2,3-dihydro-1H-1,4-benzodiazepin-2-one of this invention in admixture with a pharmaceutically acceptable carrier.

DETAILED DESCRIPTION

In Formula I, $R^1$ is H, alkyl or fluoroalkyl of 1–4 carbon atoms and up to 9 fluorine atoms; or cycloalkyl of 4–8 carbon atoms. H, methyl; H, methyl, ethyl 2,2,2-trifluoroethyl or cyclopropylmethyl are most preferred. It can, however, also be other alkyl, fluorinated alkyl or cycloalkylalkyl groups. Alkyl is preferably methyl or ethyl, and also n-propyl, isopropyl, n-butyl, isobutyl, sec.-butyl or tert.-butyl. The alkyl groups can be monofluorinated or polyfluorinated, having preferably up to 5 fluorine substituents and, most preferably, up to 3 fluorine substituents. Examples of fluorinated alkyl include fluoromethyl, difluoromethyl; trifluoromethyl; 1- or 2-fluoroethyl; 1,1-, 1,2- or 2,2-difluoroethyl; 1,1,2-, 1,2,2- or 2,2,2-trifluoroethyl; 1,1,2,2- or 1,2,2,2-tetrafluoroethyl; pentafluoroethyl; 3,3,3-trifluoropropyl; 2,2,3,3,3-pentafluoropropyl; heptafluoropropyl; 4,4,4-trifluorobutyl or nonafluorobutyl. Examples of cycloalkylalkyl groups are cyclopropylmethyl, 2-cyclopropylethyl, cyclobutylmethyl, 2-cyclobutylethyl, cyclopentylmethyl, 2-cyclopentylethyl, cyclohexylmethyl or 2-cyclohexylethyl.

$R^2$ is preferably phenyl. $R^2$ can also be monohalophenyl, preferably fluorophenyl or chlorophenyl, but also bromophenyl or iodophenyl. The halogen atom is preferably in the o-position, but it can be in the m- or p-position. Accordingly, halophenyl is preferably o-fluorophenyl or o-chlorophenyl, as well as m-fluorophenyl, p-fluorophenyl, m-chlorophenyl, p-chlorophenyl, o-, m- or p-bromophenyl, or o-, m- or p-iodophenyl. $R^2$ can also be a pyridyl, preferably 2-pyridyl, but can also be 3-pyridyl or 4-pyridyl.

$R^3$ is preferably F or Cl, but can be $NO_2$ or Br.

The invention relates particularly to compounds of Formula I in which at least one of the radicals mentioned has one of the preferred meanings indicated above. Some of these preferred groups of compounds are those of groups Ia to Ik, below, which otherwise correspond to Formula I but wherein:

Ia. $R^1$ is H, methyl, ethyl, 2,2,2-trifluoroethyl or cyclopropylmethyl;

Ib. $R^2$ is phenyl, o-fluorophenyl, o-chlorophenyl or 2-pyridyl;

Ic. $R^3$ is F, Cl or $NO_2$;

Id. $R^1$ is H, methyl, ethyl, 2,2,2-trifluoroethyl or cyclopropylmethyl and
$R^2$ is phenyl, o-fluorophenyl, o-chlorophenyl or 2-pyridyl;

Ie. $R^1$ is H, methyl or ethyl and
$R^2$ is phenyl, o-fluorophenyl, o-chlorophenyl or 2-pyridyl;

If. $R^1$ is H or methyl and
$R^2$ is phenyl, o-fluorophenyl, o-chlorophenyl or 2-pyridyl;

Ig. $R^1$ is H or methyl,
$R^2$ is phenyl, o-fluorophenyl or o-chlorophenyl and
$R^3$ is F, Cl or $NO_2$;

Ih. $R^1$ is H or methyl and
$R^2$ is phenyl or o-chlorophenyl;

Ii. $R^1$ is H and
$R^2$ is phenyl, o-fluorophenyl, o-chlorophenyl or 2-pyridyl;

Ij. $R^1$ is H or methyl,
$R^2$ is phenyl or o-chlorophenyl and
$R^3$ is F, Cl or $NO_2$; and Ik. $R^1$ is H or methyl,
$R^2$ is phenyl or o-chlorophenyl and
$R^3$ is F or Cl.

In a preparative aspect, this invention relates to processes for the preparation of the compounds of Formula I and their physiologically acceptable acid addition salts, wherein (a) a compound of Formula II

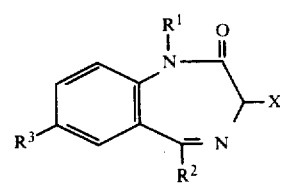

wherein X is H, M, OH, esterified OH, halogen or $NH_2$; M is Na, K, Li, Mg-halogen or $TlF_2$ and halogen is Cl, Br or I and $R^1$, $R^2$ and $R^3$ are as above, or a 4-N-oxide of a compound of Formula II (X is H), is treated with a fluorinating agent;

(b) a compound of Formula III $$\text{III}$$

wherein $X^1$ is OH, alkoxy of 1–4 carbon atoms, Cl or Br and $R^1$ and $R^3$ are as above, is reacted with a compound of Formula IV $$R^2-M \qquad \text{IV}$$

wherein $R^2$ and M are as above;

(c) a compound of Formula V $$\text{V}$$

wherein $X^2$ is H or OH and $R^1$, $R^2$ and $R^3$ are as above, is treated with an oxidizing agent;

(d) a N-oxide of Formula VI $$\text{VI}$$

wherein $R^1$, $R^2$ and $R^3$ are as above, is treated with a reducing agent;

(e) a compound of Formula VII $$\text{VII}$$

wherein $X^3$ is OH, functionally-modified OH or $R^5$—$SO_2$—; $X^4$ is H or $X^3$ and $X^4$ collectively are —CH$_2$—CHR$^4$—O—; $R^4$ is H or A; $R^5$ is alkyl or aryl of up to 10 carbon atoms substituted by up to 3 halogen atoms; A is alkyl of 1–4 carbon atoms and $R^1$, $R^2$ and $R^3$ are as above, is treated with an agent which splits out $X^3X^4$;

(f) a compound of Formula VIII $$\text{VIII}$$

wherein Q is —CF(COOH)—, —CF(COO—tert.—C$_4$H$_9$)— or —CH(O—CO—F) and $R^1$, $R^2$ and $R^3$ are as above, is cleaved by the action of heat;

(g) a compound of Formula IX $$R^2-L \qquad \text{IX}$$

wherein L is wherein one E group is H and the other E group is $X^5$, $X^5$ is OH, esterified OH or halogen, and An$^\ominus$ is an anion of a strong acid, and $R^1$, $R^2$, $R^3$ and A are as above, is cyclized;

(h) a compound of Formula X $$\text{X}$$

wherein $R^1$ and $R^2$ are as above, is treated with a halogenating or nitrating agent, and, if appropriate, an alkyl, fluorinated alkyl or cycloalkylalkyl group is introduced by treatment with an alkylating agent into a resulting compound of the formula I ($R^1$ is H) and/or a resulting base of Formula I is converted by treatment with an acid into one of its physiologically acceptable acid addition salts.

In the compounds of Formula II, X is preferably H, Cl or Br. It can, however, also be M, OH, esterified OH, I or NH$_2$. M is preferably K or Li, but can also be Na, MgCl, MgBr, MgI or TlF$_2$. If X is an esterified OH group, it is preferably an OH group which is esterified by a reactive acid residue, such as alkylsulfonyloxy having, preferably, 1-6 carbon atoms, e.g., methanesulfonyloxy or hexanesulfonyloxy, or arylsulfonyloxy having, preferably, 6-10 carbon atoms, e.g., benzenesulfonyloxy, p-toluenesulfonyloxy, 1-naphthalenesulfonyloxy or 2-naphthalenesulfonyloxy. Examples of other suitable esterified OH groups are trifluoromethanesulfonyloxy, trichloromethanesulfonyloxy, p-nitrobenzenesulfonyloxy and trifluoroacetoxy.

In compounds of Formula III, $X^1$ is preferably Cl, Br or alkoxy of 1-4 carbon atoms, preferably methoxy or ethoxy. It can, however, also be propoxy, isopropoxy, n-butoxy, isobutoxy, sec.-butoxy, tert.-butoxy, or hydroxyl.

In the compounds of Formula V, $X^2$ is preferably H. In the compounds of Formula VII, $X^3$ preferably represents OH or $R^5$—$SO_2$ wherein $R^5$ is preferably alkyl of 1-6 carbon atoms, such as methyl or ethyl; aryl of 6-10 carbon atoms, such as phenyl or p-tolyl; or halogenated alkyl, e.g., $CF_3$ or $CCl_3$. If $X^3$ is a functionally-modified OH group, this radical is preferably alkanoyloxy of 1-6 carbon atoms, e.g., acetoxy; carbamoyloxy, alkylcarbamoyloxy or dialkylcarbamoyloxy, wherein the alkyl groups have 1-4 carbon atoms in each particular case. $X^4$ is preferably H and $R^4$ is preferably H or $CH_3$. If $X^3$ and $X^4$ are collectively —$CH_2$—$CHR^4$—O—, they are, accordingly, preferably collectively —$CH_2$—$CH_2$—O— or —$CH_2$—$CH(CH_3)$—O—.

A is preferably methyl or ethyl, but can be n-propyl, isopropyl, n-butyl, isobutyl, sec.-butyl, or tert.-butyl.

If E groups are present in the compounds of the Formula IX and the E group on the N atom is H, then the E group on the C atom is preferably halogen, especially Br, or OH esterified in a reactive manner, as above. If the E group on the C atom is H, then the E group on the N atom is preferably OH or OH esterified in a reactive manner, as above, e.g., arylsulfonyloxy.

The compounds of Formula I are prepared by methods which are in themselves known, and described in the literature, for example, in works such as Houben-Weyl, Methoden der Organischen Chemie ("Methods of Organic Chemistry"), Georg-Thieme-Verlag, Stuttgart, under the reaction conditions which are known and suitable for the reactions mentioned.

The starting materials for the preparation of the compounds of Formula I can, if desired, be formed in situ so that they are not isolated from the reaction mixture but are immediately converted to form the compounds of Formula I.

Some of the starting materials of Formulae II to X are known. Those which are new, can, however, be prepared from known starting materials by known methods. For example, the fluorine-substituted starting materials of Formula III and V to X can be prepared from corresponding non-fluorinated compounds by introduction or exchange reaction of the fluorine atom, for example, by the methods described below for the fluorination of the compounds of Formula II.

The compounds of Formula I can preferably be obtained by introducing a fluorine atom into the compounds of Formula II most of which are known. Examples of suitable fluorinating agents are hydrofluoric acid, particularly in the form of a complex with pyridine, and salts thereof, for example, NaF, KF, $NH_4F$, AgF, $AgF_2$, $CoF_3$, $HgF_2$, $Hg_2F_2$ and TlF; inorganic fluorides, e.g., $SbF_3$, $SbF_5$, $ClO_3F$, $SF_5OF$, $SOF_2$ and $SF_4$; organic fluorine compounds, e.g., $CF_3OF$, $CF_2(OF)_2$, $(CF_3)_3COF$ and F—COOA, preferably F—COOC$_2$H$_5$; and tetrafluorophosphoranes, e.g., ethyltetrafluorophosphorane or phenyltetrafluorophosphorane; 2-chloro-1,1,2-trifluorotriethylamine; cyanuric fluoride and N-fluoroamides, e.g., $CH_3$—CO—NF—$CH_3$. The fluorination can be carried out by electrophilic substitution, e.g. using perchloryl fluoride and trifluoromethyl hypofluorite; by a radical mechanism, e.g., using trifluoromethyl hypofluorite and irradiation; or by nucleophilic substitution, e.g., using HF, its salts or inorganic fluorides.

The reaction can be carried out in the presence of an additional inert solvent; or an excess of the fluorinating agent can be used as the solvent. Examples of suitable inert solvents are hydrocarbons, e.g., hexane, benzene or toluene; halogenated hydrocarbons, e.g., methylene chloride, chloroform, carbon tetrachloride, trifluorochloromethane or fluorotrichloromethane; ethers, e.g., diethyl eher, tetrahydrofuran (THF), dioxane or diglyme; sulfoxides, e.g., dimethylsulfoxide (DMSO); amides, e.g., dimethylformamide (DMF) or phosphoric acid hexamethyltriamide (HMPT); nitriles, e.g., acetonitrile; or amines, e.g., triethylamine or pyridine. The reaction temperatures are between about $-100°$ and $+170°$, preferably between $-80°$ and $+150°$, depending on the method used.

A preferred method of fluorination consists of replacing the halogen atom in a halogen compound of Formula II (X is halogen) by fluorine, for example by reaction with HF, or its salts, preferably silver fluoride; inorganic fluorides, e.g., $SbF_3$, $SbF_5$, or tetraethylammonium fluoride. Acetonitrile or pyridine are the preferred solvents for this variation of the fluorination process; the reaction is preferably carried out at temperatures between about 0° and 150°, particularly at room temperature. The reactivity of the fluoride ion in potassium fluoride is increased by adding a catalytic quantity of a "crown ether," for example, 1,4,7,10,13,16-hexaoxacyclooctadecane. In some cases it can be advantageous to add phase transfer catalysts, such as hexadecyl tributylphosphonium bromide. An electrophilic fluorination is preferably carried out by first converting the starting compound II (X is H) into a corresponding metal derivative (II, X is M), for example, by reaction with organolithium compound, e.g., n-butyl lithium, or a strong base, e.g., potassium tert.-butylate. It is possible subsequently to carry out a reaction under mild conditions with perchloryl fluoride or trifluoromethyl hypofluorite.

A photofluorination of II (X is H) can be carried out with $CF_3OF$ in liquid HF or in fluorinated solvents, such as $CFCl_3$, preferably at low temperatures of about $-80°$.

The amino group in amino compounds of Formula II (X is $NH_2$) can be replaced by a fluorine atom by reacting these compounds with salts or esters of nitrous acid in the presence of HF, for example, in the system HF/pyridine, preferably at temperatures between about $-10°$ and 20°.

A further variation of the fluorination process consists of metalizing a compound of Formula II (X is H) by Tl(CF$_3$COO)$_3$, reacting the resulting product [II, X is Tl(CF$_3$COO)$_2$] with a fluoride such as KF to give II (X is TlF$_2$) and treating this product with BF$_3$-etherate.

It is also possible to introduce a fluorine atom into a compound of Formula II (X is H) by electrolysis in liquid HF, preferably in the presence of an inorganic fluoride, e.g., $SbF_3$, preferably at current densities between 0.01 and 0.03 a/cm² and voltages between 4 and 8 volts.

It is also possible to fluorinate 1—R¹—5—R²—7—R³—2,3-dihydro-1H-benzodiazepin-2-one 4-N-oxides [4-N-oxides of compounds of the formula II (X is H)], preferably in the presence of an oxygen acceptor, e.g., SbF₃, or SbCl₃. In the course of the reaction, the O atom in the 4-position is removed, presumably via a cyclic mechanism, and a F atom is introduced into the 3-position.

The compounds of Formula I can also be obtained by reacting the benzodiazepinones of Formula III with organometallic compounds of Formula IV. The compounds of Formula III are new, but they can be readily obtained by the fluorination methods indicated above, from corresponding substances having a substituent X in the 3-position instead of the fluorine atom.

The compounds of Formula IV, for example, phenyl lithium, phenylmagnesium chloride, bromide or iodide, o-, m-, or p-fluorophenylmagnesium chloride, bromide or iodide, or pyridyllithium are known. The reaction is preferably carried out in the presence of an inert solvent, preferably the solvent in which organometallic compound IV was prepared before the reaction, for example, an ether, such as diethyl ether, diisopropyl ether, di-n-butyl ether, THF or dioxane, mixed, if desired, with hydrocarbons, such as petroleum ether or hexane. The reaction temperatures are suitably between about −20 and +100°, preferably between 30° and 80°. After the reaction, the product is hydrolyzed in the customary manner, for example, using ammonium chloride solution.

The compounds of Formula I can also be obtained by oxidizing the benzodiazepines of Formula V. These starting materials are also new, but can be obtained by fluorinating the corresponding compounds which carry the radical X instead of a fluorine atom. Preferred oxidizing agents for the benzodiazepines V (X² is H) are potassium permanganate and selenium dioxide and, for the 2-hydroxybenzodiazepines (V, X² is OH), chromium trioxide, chromates or dichromates. The reaction is generally carried out in the solvents which are customary for oxidation of this kind, for example, in ketones, e.g., acetone; bases, e.g., pyridine, or mixtures thereof, at temperatures between about 0° and 120°, preferably between 20° and 100°.

The compounds of Formula I can also be obtained by reducing corresponding 4-N-oxides of Formula VI. Examples of suitable reducing agents are SOCl₂, PCl₃, or other phosphorus (III) compounds, including trialkyl phosphites, triaryl phosphites or triarylphosphines, e.g., triphenylphosphine. It is also possible to treat the oxides with hydrogen in the presence of a noble metal catalyst. The solvents used in the reduction are those which are customary, for example, hydrocarbons, e.g., benzene; ethers, e.g., THF and dioxane; or an excess of the reducing agent. The temperatures used for the reduction are preferably between 0° and 120°, most preferably between 60° and 110°.

The compounds of Formula I can also be prepared by splitting a molecule X³X⁴ out of a compound of Formula VII. The compound to be split out can be water, an alcohol, an acid or an alkylene oxide, e.g., ethylene oxide. Suitable agents for splitting out X³X⁴ are dehydrating agents, e.g., POCl₃, or other inorganic acid chlorides; carbodiimides, e.g., dicyclohexylcarbodiimide, if X³X⁴ is water; bases, for example, alcoholates, e.g., K tert.-butylate; matal hydrides, e.g., NaH, or tertiary amines, such as triethylamine if X³X⁴ is an acid; or carboxylic acid anhydride/carboxylic acid salt, systems, e.g., acetic anhydride/sodium acetate, if X³X⁴ is an alkylene oxide. The elimination reaction can be carried out in the presence of an additional inert solvent, e.g., a halogenated hydrocarbon, such as methylene chloride, or an amide, such as DMF, at temperatures between about 0° and 150°.

The compounds of Formula I can also be obtained by cleaving compounds of Formula VIII by heat. These are substances which correspond to Formula I, but which either bear a carboxylic acid or carboxylic acid ester group in the 3-position or have an —O—CO—F group instead of the fluorine atom. The cleavage by heat is carried out at temperatures between about 40° and 180°, preferably between 60° and 150°. An additional inert, preferably high-boiling solvent, e.g., a base, such as pyridine, an amide, such as DMF, or a sulfoxide, such as DMSO can be used as can a catalyst, for example, a metal oxide, such as CuO, or a strong acid, such as p-toluenesulfonic acid. During the cleavage by heat, CO₂ and, if Q is —CF(COO—tert.—C₄H₉), isobutylene, are split out.

The desired 3-fluorobenzodiazepinones can also be obtained by cyclizing compounds of Formulae IXa-IXd,

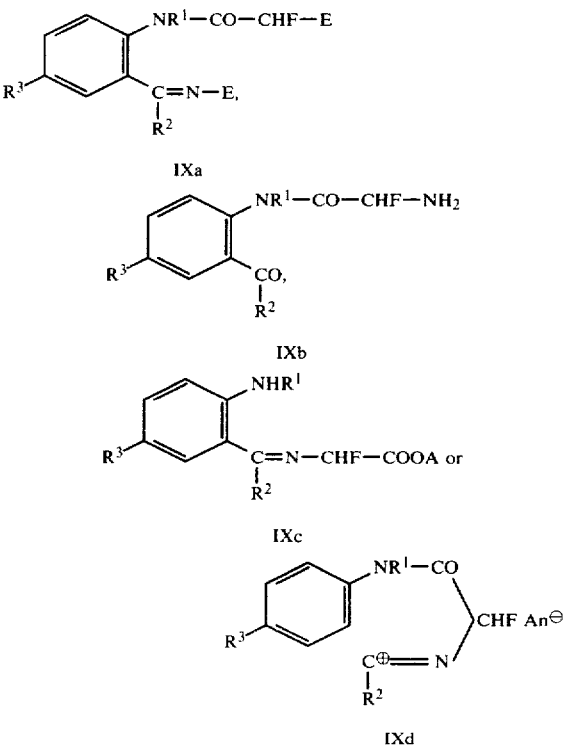

IXa and IXc are preferred for the cyclization.

The starting materials of Formula IX are new. Compounds of Formula IXa can, for example, be prepared by acylating corresponding amino derivatives of the formula 2—(NHR¹)—5—R³—C₆H₃—CR²=N—E using acid halides of the formula E—CHF—CO—Hal The aminoketones of Formula IXb can be obtained, for example, by acylating aminoketones of the formula 2—NHR¹—5—R³—C₆H₃—CO—R² using α-bromo-α fluoroacetyl bromide and subsequently reacting with ammonia or an ammonia donor, e.g., hexamethylenetetramine, by reducing corresponding azidoketones or by solvolyzing corresponding compounds having a protected primary amino group, for example, phthalimidoketones. Preferably, the compounds of Formula IXb are prepared in situ. The reaction of ketones of the formula 2—NHR$^1$—5—R$^3$C$_6$H$_3$—CO—R$^2$ with α-Hal-α-fluoroorthoacetic acid trialkyl esters and the subsequent rearrangement of the resulting product under the influence of liquid ammonia leads to compounds IXc. The compounds IXd are preferably prepared in situ by reacting an amide of the formula p—R$^3$—C$_6$H$_4$—NR$^1$—CO—CHFHal with a nitrile of the formula R$^2$—CN in the presence of a Lewis acid, e.g., SnCl$_4$.

In the cyclization of the compounds of the Formula IX, water, an alcohol or an acid can be split off. Accordingly, the cyclization is preferably carried out in the presence of a dehydrating agent or a base, as well as by heating in the absence or presence of an inert solvent. Examples of suitable dehydrating agents are inorganic or organic acid halides, such as p-toluenesulfochloride or POCl$_3$; and carbodiimides, such as dicyclohexylcarbodiimide. Examples of suitable bases are alkali metal hydroxides, such as NaOH; tertiary amines, such as pyridine, triethylamine, 1,5-diazabicyclo-[4,3,0]-non-5-ene and similar bis-tertiary, bicyclic bases, as well as 2-methylimidazole or acetic acid. Examples of suitable inert solvents are alcohols, e.g., methanol, ethanol or butanol; ethers, e.g., diethyl ether or THF; amides, such as DMF; sulfoxides, such as DMSO; halogenated hydrocarbons, such as methylene chloride or chloroform; or hydrocarbons, such as benzene or toluene. An excess of the cyclizing agent can also be used as the solvent, for example, pyridine.

The cyclization is preferably carried out at temperatures between about −50° and +150°.

Compounds of Formula I can also be obtained by halogenating or nitrating benzodiazepinones of Formula X, which are readily obtainable from the corresponding compounds which carry a substituent X other than fluorine, in the 3-position. Chlorination or bromination of these substances is carried out in the customary manner, for example, by the action of chlorine, bromine or inorganic chlorides or bromides, e.g., sulfuryl chloride, in inert solvents, e.g., halogenated hydrocarbons, for example, CCl$_4$; or nitrobenzene. Catalysts, such as iron turnings, or Lewis acids, such as AlCl$_3$ or FeCl$_3$, can be present. The halogenation is carried out in the temperature range between about 0° and 100°, preferably between 20° and 80°. Owing to the sensitivity of the end product to acids, it is advisable to exercise particular care in removing the hydrogen halide formed.

The nitration of compounds of the Formula X is preferably carried out using derivatives of nitric acid, for example, acyl nitrates, e.g., acetyl nitrate or benzoyl nitrate, which can be formed in situ, for example, from acetic anhydride or benzoyl chloride and heavy metal nitrates; metal nitrates, for example, in the presence of Lewis acids; alkyl nitrates; nitryl halides, e.g., NO$_2$F, NO$_2$Cl, NO$_2$Br, NO$_2$AsF$_6$ or NO$_2$SbF$_6$; nitrogen oxides, e.g., N$_2$O$_3$ or N$_2$O$_4$, and their complexes with Lewis acids, e.g., BF$_3$ or AlCl$_3$. Examples of solvents which are suitable for the nitration are halogenated hydrocarbons, e.g., CCl$_4$; nitriles, e.g., acetonitrile; nitroalkanes, e.g., nitromethane; or sulfolane.

If desired, another R$^1$ can be introduced into a resulting compound of Formula I (R$^1$ is H) by known methods of alkylation. Examples of suitable alkylating agents are halides of the formula R$^1$-Hal, e.g., methyl chloride, bromide or iodide; ethyl chloride, bromide or iodide; 2,2,2-trifluoroethyl chloride, bromide or iodide; cyclopropylmethyl chloride, bromide or iodide; and the corresponding sulfates or sulfonates, e.g., dimethyl sulfate or p-toluenesulfonic acid methyl ester. It is preferable to add a base, for example, an alkali metal alcoholate, e.g., sodium methylate or ethylate or potassium tert.-butylate; an alkali metal hydride, e.g., sodium hydride or lithium hydride; an alkali metal hydroxide, e.g., sodium hydroxide or potassium hydroxide; an alkali metal amide, e.g., lithium amide, sodium amide or potassium amide; or an organometallic compound, e.g., butyl lithium, or phenyl lithium or phenyl magnesium bromide. Examples of suitable solvents for the alkylation are hydrocarbons, e.g., benzene, toluene or xylene; ethers, e.g., diethyl ether, diglyme or THF; and amides, e.g., DMF, HMPT, dimethylacetamide or N-methylpyrrolidone. The alkylation is suitably carried out at temperatures between 0° and 100°, preferably between 20° and 80°.

A base of Formula I can be converted into an acid addition salt in the customary manner by means of an acid. Acids which can be used for this reaction are those which give physiologically acceptable salts. Thus, inorganic acids can be used, for example, sulfuric acid; nitric acid; hydrohalic acids, e.g., hydrochloric acid, hydrobromic acid; phosphoric acids, e.g., orthophosphoric acid; and sulfamic acid. Organic acids can also be used including aliphatic, alicyclic, araliphatic, aromatic or heterocyclic, monobasic or polybasic carboxylic or sulfonic acids, e.g., formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid and naphthalenemonosulfonic acids and naphthalenedisulfonic acids.

If desired, the free bases of Formula I can be liberated from their salts by treatment with strong bases, such as sodium hydroxide, potassium hydroxide, sodium carbonate or potassium carbonate.

Compounds of Formula I contain a center of asymmetry. Therefore, they can be obtained as racemates or can also be obtained in an optically active form, if optically active starting materials are used. If desired, racemates can be resolved into their optical antipodes by mechanical or chemical means using known methods. It is preferred to form diastereomers from the racemate by reaction with an optically active resolving agent. Examples of suitable resolving agents are optically active carrier materials for chromatography, for example, polyesters, polyamides or modified celluloses; or optically active acids, e.g., tartaric acid, dibenzoyltartaric acid, diacetyltartaric acid, camphorsulfonic acids, mandelic acid, malic acid or lactic acid.

These compounds of Formula I are well tolerated and possess valuable pharmacological properties, particularly, effects on the central nervous system. They display central nervous system depressant effects. Muscle-relaxing, anticonvulsive and anxiolytic effects are particularly pronounced. The muscle-relaxing effect can be demonstrated, for example, on rats in the muscle relaxation pair test [for method, see H. Mueller-Calgan et al., described in H. P. Zippel (Ed.), Memory and Transfer of Information, Plenum Press (New York-London), pages 97–100 (1973)] using the experimentatal scheme of A. Ribbentrop and W. Schaumann [Arzneimittelforschung, Volume 15, pages 863–868 (1965)].

The anti-convulsive effect can be demonstrated, for example, on rats given cramp-inducing and lethal doses of pentylenetetrazole. Narcosis-boosting properties are demonstrated, for example, on mice or rats, by the method of Janssen et al. (Journal of Medicinal and Pharmaceutical Chemistry, Volume 1, 1959, pages 281–297). Effects which prolong narcosis are also observed. Furthermore, the substances have a tranquillizing effect on the spontaneous activity and threatening behavior of Rhesus monkeys, see H. Mueller-Calgan, Activ. nerv. sup. (Prague), Volume 16, pages 62–64 (1974).

The new substances are also distinguished by lower sensitivity to solvolysis and increased stability toward moisture in comparison to known 3-chloro compounds, such as 3-chlorodiazepam.

The compounds of Formula I and their physiologically acceptable acid addition salts can be used as medicaments and also as intermediate products for the preparation of other medicaments. For example, they can be converted by acid hydrolysis into the corresponding 3-hydroxy compounds which, in turn, have valuable pharmacological, for example, tranquilizing, properties, such as, for example, 3-hydroxydiazepam (Temazepam).

The new compounds of Formula I and their physiologically acceptable acid addition salts can be used, mixed with solid, liquid and/or semi-liquid medicinal excipients, as medicaments in human or veterinary medicine. Possible excipients are organic or inorganic substances which are suitable for enteral, oral or parenteral administration and which do not react with the new compounds, such as, for example, water, vegetable oils, polyethylene glycols, gelatine, lactose, starch, magnesium stearate or talc. Tablets, dragees, capsules, syrups, elixirs or suppositories are suitable for enteral administration. Solutions, preferably oily or aqueous solutions, and also suspensions, emulsions or implants, are in particular used for parenteral administration. These preparations can be sterilized and/or can be treated with auxiliaries, such as preservatives, stabilizers and/or wetting agents, salts for regulating the osmotic pressure, buffer substances, dyestuffs, flavorings and/or aroma substances. If desired, they can also contain one or more other active compounds.

The 3-fluoro-2,3-dihydro-1,4-benzodiazepin-2-ones of this invention are central nervous system depressants, useful for inducing muscle-relaxant, anti-convulsant and anxiolytic effects in mammals, especially in humans. In this respect, they are administered, in admixture with a pharmaceutically acceptable carrier, to the afflicted animal, similarly to the known drugs diazepam, chlordiazepoxide, nitrazepam or temazepam.

The substances according to the invention are preferably administered in doses between about 0.1 and 50 mg., particularly between 1 and 20 mg per dosage unit. The daily dose is preferably between about 0.002 and 1 mg/kg of body weight. Oral administration is preferred.

Each of the compounds of Formula I mentioned in the examples which follow is particularly suitable for the production of pharmaceutical preparations.

In the examples which follow, "customary working up" denotes: water is added, if necessary; the mixture is extracted with methylene chloride, chloroform or diethyl ether; the organic phase is separated off, dried over sodium sulfate, filtered and evaporated and the residue is purified by chromatography over silica gel and/or by crystallization.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

20 ml. of benzene are added, under nitrogen, to a mixture of 0.1 mole of n-butyl lithium in 20 ml. of hexane and 10 g. of diisopropylamine are added dropwise at 0°. A solution of 28.5 g. of 1-methyl-5-phenyl-7-chloro-2,3-dihydro-1H-1,4-benzodiazepin-2-one (diazepam) in 800 ml. of benzene is then added. After stirring for 1 hour at about 20°, the mixture is evaporated and the residue is taken up in 300 ml. of THF and a solution of 22 g. $ClO_3F$ in 60 ml. of THF is added dropwise. After stirring for 2 hours, the mixture is evaporated and worked up in the customary manner. The product is 1-methyl-3-fluoro-5-phenyl-7-chloro-2,3-dihydro-1H-1,4-benzodiazepin-2-one (3-fluorodiazepam), m.p. 152°–154°.

EXAMPLES 2–13

The following are obtained by the method of Example 1 from the corresponding compounds of Formula II (X is H):

2. 1-Methyl-3-fluoro-5-o-fluorophenyl-7-chloro-2,3-dihydro-1H-1,4-benzodiazepin-2-one.
3. 1-Methyl-3-fluoro-5-m-fluorophenyl-7-chloro-2,3-dihydro-1H-1,4-benzodiazepin-2-one.
4. 1-Methyl-3-fluoro-5-p-fluorophenyl-7-chloro-2,3-dihydro-1H-1,4-benzodiazepin-2-one.
5. 1-Methyl-3-fluoro-5-o-chlorophenyl-7-chloro-2,3-dihydro-1H-1,4-benzodiazepin-2-one.
6. 1-Methyl-3-fluoro-5-m-chlorophenyl-7-chloro-2,3-dihydro-1H-1,4-benzodiazepin-2-one.
7. 1-Methyl-3-fluoro-5-p-chlorophenyl-7-chloro-2,3-dihydro-1H-1,4-benzodiazepin-2-one.
8. 1-Methyl-3-fluoro-5-o-bromophenyl-7-chloro-2,3-dihydro-1H-1,4-benzodiazepin-2-one.
9. 1-Methyl-3-fluoro-5-m-bromophenyl-7-chloro-2,3-dihydro-1H-1,4-benzodiazepin-2-one.
10. 1-Methyl-3-fluoro-5-p-bromophenyl-7-chloro-2,3-dihydro-1H-1,4-benzodiazepin-2-one.
11. 1-Methyl-3-fluoro-5-(2-pyridyl)-7-chloro-2,3-dihydro-1H-1,4-benzodiazepin-2-one.
12. 1-Methyl-3-fluoro-5-(3-pyridyl)-7-chloro-2,3-dihydro-1H-1,4-benzodiazepin-2-one.
13. 1-Methyl-3-fluoro-5-(4-pyridyl)-7-chloro-2,3-dihydro-1H-1,4-benzodiazepin-2-one.

EXAMPLE 14

28.5 g. of Diazepam are dissolved in 200 ml. of DMF and 12 g. K tert.-butylate are added at 0° with stirring. After stirring for 15 minutes, the mixture is cooled to −40° and $CF_3OF$ is introduced, using nitrogen as carrier gas, until the mixture is saturated. After stirring for one hour at −40°, the mixture is allowed to reach 20°, whereupon a stream of nitrogen is passed through the solution for 20 minutes and it is stirred into ice water and worked up in the customary manner to give 3-fluorodiazepam, m.p. 152°–154°.

EXAMPLE 15

2.85 g. of Diazepam are dissolved in 200 ml. of $CFCl_3$ and the solution is irradiated with UV light at −80°, with stirring while 1.1 g. of $CF_3OF$ is added over the course of one hour. The mixture is evaporated under a stream of nitrogen and the residual oil is purified chromatographically to give 3-fluorodiazepam, m.p. 152°–154°.

EXAMPLE 16

3.7 g. of 1-(2,2,2-trifluoroethyl)-5-phenyl-7-chloro-2,3-dihydro-1H-1,4-benzodiazepin-2-one 4-N-oxide are added to 10 ml. of fluoroformic acid ethyl ester; the mixture is warmed to 70° for 20 minutes with stirring and is evaporated to give 1-(2,2,2-trifluoroethyl)-3-fluoro-5-phenyl-7-chloro-2,3-dihydro-1H-1,4-benzodiazepin-2-one.

EXAMPLES 17–27

The following are obtained by the method of Example 16 from the corresponding 4-N-oxides:
17. 1-(2,2,2-Trifluoroethyl)-3-fluoro-5-o-fluorophenyl-7-chloro-2,3-dihydro-1H-1,4-benzodiazepin-2-one.
18. 1-(2,2,2-Trifluoroethyl)-3-fluoro-5-o-chlorophenyl-7-chloro-2,3-dihydro-1H-1,4-benzodiazepin-2-one.
19. 1-(2,2,2-Trifluoroethyl)-3-fluoro-5-(2-pyridyl)-7-chloro-2,3-dihydro-1H-1,4-benzodiazepin-2-one.
20. 1-(2,2,2-Trifluoroethyl)-3-fluoro-5-phenyl-7-bromo-2,3-dihydro-1H-1,4-benzodiazepin-2-one.
21. 1-(2,2,2-Trifluoroethyl)-3-fluoro-5-o-fluorophenyl-7-bromo-2,3-dihydro-1H-1,4-benzodiazepin-2-one.
22. 1-(2,2,2-Trifluoroethyl)-3-fluoro-5-o-chlorophenyl-7-bromo-2,3-dihydro-1H-1,4-benzodiazepin-2-one.
23. 1-(2,2,2-Trifluoroethyl)-3-fluoro-5-(2-pyridyl)-7-bromo-2,3-dihydro-1H-1,4-benzodiazepin-2-one.
24. 1-(2,2,2-Trifluoroethyl)-3-fluoro-5-phenyl-7-nitro-2,3-dihydro-1H-1,4-benzodiazepin-2-one.
25. 1-(2,2,2-Trifluoroethyl)-3-fluoro-5-o-fluorophenyl-7-nitro-2,3-dihydro-1H-1,4-benzodiazepin-2-one.
26. 1-(2,2,2-Trifluoroethyl)-3-fluoro-5-o-chlorophenyl-7-nitro-2,3-dihydro-1H-1,4-benzodiazepin-2-one.
27. 1-(2,2,2-Trifluoroethyl)-3-fluoro-5-(2-pyridyl)-7-nitro-2,3-dihydro-1H-1,4-benzodiazepin-2-one.

EXAMPLE 28

(a) A mixture of 2.87 g. of 5-phenyl-7-chloro-2,3-dihydro-1H-1,4-benzodiazepin-2-one 4-N-oxide, 10 ml. of anhydrous HF and 0.1 g. of $SbCl_5$ is stirred for 24 hours at 3° to 5°. The mixture is evaporated and is stirred into ice cold sodium carbonate solution and worked up in the customary manner to give 3-fluoro-5-phenyl-7-chloro-2,3-dihydro-1H-1,4-benzodiazepin-2-one, m.p. 235° (decomposition).

(b) 0.6 g. of sodium methylate is added at 20° to a solution of 2.89 g. of 3-fluoro-5-phenyl-7-chloro-2,3-dihydro-1H-1,4-benzodiazepin-2-one in 35 ml. of DMF. The mixture is stirred for 30 minutes at 60° and is cooled to 30°, a solution of 1.9 g. of $CH_3I$ in 10 ml. of DMF is added and the mixture is stirred overnight. It is poured onto ice and worked up in the customary manner to give 3-fluorodiazepam, m.p. 152°–154°.

(c) 0.64 g. of sodium methylate is added, with stirring, to a solution of 3.23 g. of 3-fluoro-5-phenyl-7-chloro-2,3-dihydro-1H-1,4-benzodiazepin-2-one in 100 ml. of toluene. After distilling off 15 ml. of toluene, the mixture is cooled to 60° and 1 ml. of dimethyl sulfate is added with stirring. The mixture is stirred for 1 hour more at 60° and is filtered while hot; cyclohexane is added to give, on cooling, 3-fluorodiazepam, m.p. 152°–154°.

(d) A solution of phenyl lithium, obtained from 0.23 g. of lithium and 2.7 g. of bromobenzene in 20 ml. of ether, is added dropwise at 10°–15°, under nitrogen, to a solution of 2.89 g. of 3-fluoro-5-phenyl-7-chloro-2,3-dihydro-1H-1,4-benzodiazepin-2-one in 100 ml. of THF. 1.9 g. of $CH_3I$ are added dropwise while stirring and passing in nitrogen and the mixture is stirred for 6 hours at 20°. After evaporating and working up in the customary manner, 3-fluorodiazepam is obtained, m.p. 152°–154°.

EXAMPLES 29–40

The following are obtained by the method of Example 28 from the corresponding 4-N-oxides:
29. 3-Fluoro-5-o-fluorophenyl-7-chloro-2,3-dihydro-1H-1,4-benzodiazepin-2-one.
30. 3-Fluoro-5-m-fluorophenyl-7-chloro-2,3-dihydro-1H-1,4-benzodiazepin-2-one.
31. 3-Fluoro-5-p-fluorophenyl-7-chloro-2,3-dihydro-1H-1,4-benzodiazepin-2-one.
32. 3-Fluoro-5-o-chlorophenyl-7-chloro-2,3-dihydro-1H-1,4-benzodiazepin-2-one, m.p. 220° (decomposition).
33. 3-Fluoro-5-m-chlorophenyl-7-chloro-2,3-dihydro-1H-1,4-benzodiazepin-2-one.
34. 3-Fluoro-5-p-chlorophenyl-7-chloro-2,3-dihydro-1H-1,4-benzodiazepin-2-one.
35. 3-Fluoro-5-o-bromophenyl-7-chloro-2,3-dihydro-1H-1,4-benzodiazepin-2-one.
36. 3-Fluoro-5-m-bromophenyl-7-chloro-2,3-dihydro-1H-1,4-benzodiazepin-2-one.
37. 3-Fluoro-5-p-bromophenyl-7-chloro-2,3-dihydro-1H-1,4-benzodiazepin-2-one.
38. 3-Fluoro-5-(2-pyridyl)-7-chloro-2,3-dihydro-1H-1,4-benzodiazepin-2-one.
39. 3-Fluoro-5-(3-pyridyl)-7-chloro-2,3-dihydro-1H-1,4-benzodiazepin-2-one.
40. 3-Fluoro-5-(4-pyridyl)-7-chloro-2,3-dihydro-1H-1,4-benzodiazepin-2-one.

EXAMPLE 41

3.36 g. of 1-methyl-5-o-chlorophenyl-7-chloro-2,3-dihydro-1H-1,4-benzodiazepin-2-one 4-N-oxide, obtainable from 2-(α-iodo-N-methyl-acetamido)-2',5'-dichloro-benzophenone oxime and pyridine, are warmed with 3 ml. of acetic anhydride and 7 g. of $SbF_3$ for one hour at 130°. After cooling, the mixture is taken up in a little DMF and is stirred into an ice cold solution of sodium potassium tartrate in dilute sodium hydroxide solution. The mixture is worked up in the customary manner using chloroform. The product is 1-methyl-3-fluoro-5-o-chlorophenyl-7-chloro-2,3-dihydro-1H-1,4-benzodiazepin-2-one.

EXAMPLE 42

First, 1.2 of KF and then 2.9 g. of 3-hydroxy-5-phenyl-7-chloro-2,3-dihydro-1H-1,4-benzodiazepin-2-one are added to a mixture of 35 g. of HF and 15 ml. of pyridine and the mixture is stirred for 1 hour more. Working up in the customary manner using sodium carbonate solution/ethyl acetate gives 3-fluoro-5-phenyl-7-chloro-2,3-dihydro-1H-1,4-benzodiazepin-2-one, m.p. 235° (decomposition).

EXAMPLE 43

To 5.4 g. of 1,4,7,10,13,16-hexaoxacyclooctadecane dissolved in 50 ml. of dry acetonitrile is added, with stirring, 1.4 g. of anhydrous KF. After 30 minutes, 4.95 g. of 1-cyclopropylmethyl-3-p-toluenesulfonyloxy-5-phenyl-7-chloro-2,3-dihydro-1H-1,4-benzodiazepin-2-one, obtainable by tosylation of the 3-hydroxy compound, in 50 ml. of dry acetonitrile are added. The mixture is stirred for 2 hours more and is worked up in the customary manner to give 1-cyclopropylmethyl-3-fluoro-5-phenyl-7-chloro-2,3-dihydro-1H-1,4-benzodiazepin-2-one.

EXAMPLES 44–54

The following are obtained by the method of Example 43 from the corresponding compounds of the Formula II (X is p-toluenesulfonyloxy):
44. 1-Cyclopropylmethyl-3-fluoro-5-o-fluorophenyl-7-chloro-2,3-dihydro-1H-1,4-benzodiazepin-2-one.
45. 1-Cyclopropylmethyl-3-fluoro-5-o-chlorophenyl-7-chloro-2,3-dihydro-1H-1,4-benzodiazepin-2-one.
46. 1-Cyclopropylmethyl-3-fluoro-5-(2-pyridyl)-7-chloro-2,3-dihydro-1H-1,4-benzodiazepin-2-one.
47. 1-Cyclopropylmethyl-3-fluoro-5-phenyl-7-bromo-2,3-dihydro-1H-1,4-benzodiazepin-2-one.
48. 1-Cyclopropylmethyl-3-fluoro-5-o-fluorophenyl-7-bromo-2,3-dihydro-1H-1,4-benzodiazepin-2-one.
49. 1-Cyclopropylmethyl-3-fluoro-5-o-chlorophenyl-7-bromo-2,3-dihydro-1H-1,4-benzodiazepin-2-one.
50. 1-Cyclopropylmethyl-3-fluoro-5-(2-pyridyl)-7-bromo-2,3-dihydro-1H-1,4-benzodiazepin-2-one.
51. 1-Cyclopropylmethyl-3-fluoro-5-phenyl-7-nitro-2,3-dihydro-1H-1,4-benzodiazepin-2-one.
52. 1-Cyclopropylmethyl-3-fluoro-5-o-fluorophenyl-7-nitro-2,3-dihydro-1H-1,4-benzodiazepin-2-one.
53. 1-Cyclopropylmethyl-3-fluoro-5-o-chlorophenyl-7-nitro-2,3-dihydro-1H-1,4-benzodiazepin-2-one.
54. 1-Cyclopropylmethyl-3-fluoro-5-(2-pyridyl)-7-nitro-2,3-dihydro-1H-1,4-benzodiazepin-2-one.

EXAMPLE 55

A solution of 31.9 g. of 3-chlorodiazepam, or 36.4 g. of 3-bromodiazepam, in 160 ml. of acetonitrile is added dropwise, while stirring, to a suspension of 13.7 g. of AgF in 700 ml. of acetonitrile. AgCl (or AgBr) is precipitated. After stirring for 3 hours at 20°, the mixture is filtered through a kieselguhr filter and the filtrate is evaporated and worked up in the customary manner. This gives 3-fluorodiazepam, m.p. 152°–154°.

EXAMPLES 56–70

The following are obtained by the method of Example 55 from the corresponding 3-chloro compounds, using AgF:
56. 1-Ethyl-3-fluoro-5-phenyl-7-chloro-2,3-dihydro-1H-1,4-benzodiazepin-2-one.
57. 1-n-Propyl-3-fluoro-5-phenyl-7-chloro-2,3-dihydro-1H-1,4-benzodiazepin-2-one.
58. 1-Isopropyl-3-fluoro-5-phenyl-7-chloro-2,3-dihydro-1H-1,4-benzodiazepin-2-one.
59. 1-n-Butyl-3-fluoro-5-phenyl-7-chloro-2,3-dihydro-1H-1,4-benzodiazepin-2-one.
60. 1-Isobutyl-3-fluoro-5-phenyl-7-chloro-2,3-dihydro-1H-1,4-benzodiazepin-2-one.
61. 1-sec.-Butyl-3-fluoro-5-phenyl-7-chloro-2,3-dihydro-1H-1,4-benzodiazepin-2-one.
62. 1-tert.-Butyl-3-fluoro-5-phenyl-7-chloro-2,3-dihydro-1H-1,4-benzodiazepin-2-one.
63. 1-Cyclopropylmethyl-3-fluoro-5-phenyl-7-chloro-2,3-dihydro-1H-1,4-benzodiazepin-2-one.
64. 1-(2-Cyclopropylethyl)-3-fluoro-5-phenyl-7-chloro-2,3-dihydro-1H-1,4-benzodiazepin-2-one.
65. 1-Cyclobutylmethyl-3-fluoro-5-phenyl-7-chloro-2,3-dihydro-1H-1,4-benzodiazepin-2-one.
66. 1-(2-Cyclobutylethyl)-3-fluoro-5-phenyl-7-chloro-2,3-dihydro-1H-1,4-benzodiazepin-2-one.
67. 1-Cyclopentylmethyl-3-fluoro-5-phenyl-7-chloro-2,3-dihydro-1H-1,4-benzodiazepin-2-one.
68. 1-(2-Cyclopentylethyl)-3-fluoro-5-phenyl-7-chloro-2,3-dihydro-1H-1,4-benzodiazepin-2-one.
69. 1-Cyclohexylmethyl-3-fluoro-5-phenyl-7-chloro-2,3-dihydro-1H-1,4-benzodiazepin-2-one.
70. 1-(2-Cyclohexylethyl)-3-fluoro-5-phenyl-7-chloro-2,3-dihydro-1H-1,4-benzodiazepin-2-one.

EXAMPLE 71

1.5 g. of AgF are added to a solution of 3.17 g. of 3-chloronitrazepam, or 4.09 g. of 3-iodonitrazepam, in 200 ml. of acetonitrile and the mixture is stirred for 3 hours. Working up in the customary manner give 3-fluoronitrazepam, m.p. 218° (decomposition).

EXAMPLES 72–96

The following are obtained following the procedure of Example 71 from the corresponding 3-chloro compounds:
72. 3-Fluoro-5-o-fluorophenyl-7-nitro-2,3-dihydro-1H-1,4-benzodiazepin-2-one, m.p. 218°–219.5°.
73. 3-Fluoro-5-m-fluorophenyl-7-nitro-2,3-dihydro-1H-1,4-benzodiazepin-2-one.
74. 3-Fluoro-5-p-fluorophenyl-7-nitro-2,3-dihydro-1H-1,4-benzodiazepin-2-one.
75. 3-Fluoro-5-o-chlorophenyl-7-nitro-2,3-dihydro-1H-1,4-benzodiazepin-2-one.
76. 3-Fluoro-5-m-chlorophenyl-7-nitro-2,3-dihydro-1H-1,4-benzodiazepin-2-one.
77. 3-Fluoro-5-p-chlorophenyl-7-nitro-2,3-dihydro-1H-1,4-benzodiazepin-2-one.
78. 3-Fluoro-5-o-bromophenyl-7-nitro-2,3-dihydro-1H-1,4-benzodiazepin-2-one.
79. 3-Fluoro-5-m-bromophenyl-7-nitro-2,3-dihydro-1H-1,4-benzodiazepin-2-one.
80. 3-Fluoro-5-p-bromophenyl-7-nitro-2,3-dihydro-1H-1,4-benzodiazepin-2-one.
81. 3-Fluoro-3-(2-pyridyl)-7-nitro-2,3-dihydro-1H-1,4-benzodiazepin-2-one.
82. 3-Fluoro-5-(3-pyridyl)-7-nitro-2,3-dihydro-1H-1,4-benzodiazepin-2-one.
83. 3-Fluoro-5-(4-pyridyl)-7-nitro-2,3-dihydro-1H-1,4-benzodiazepin-2-one.
84. 1-Methyl-3-fluoro-5-phenyl-7-nitro-2,3-dihydro-1H-1,4-benzodiazepin-2-one.
85. 1-Methyl-3-fluoro-5-o-fluorophenyl-7-nitro-2,3-dihydro-1H-1,4-benzodiazepin-2-one, m.p. 227.5°–229°.
86. 1-Methyl-3-fluoro-5-m-fluorophenyl-7-nitro-2,3-dihydro-1H-1,4-benzodiazepin-2-one.
87. 1-Methyl-3-fluoro-5-p-fluorophenyl-7-nitro-2,3-dihydro-1H-1,4-benzodiazepin-2-one.
88. 1-Methyl-3-fluoro-5-o-chlorophenyl-7-nitro-2,3-dihydro-1H-1,4-benzodiazepin-2-one.

89. 1-Methyl-3-fluoro-5-m-chlorophenyl-7-nitro-2,3-dihydro-1H-1,4-benzodiazepin-2-one.
90. 1-Methyl-3-fluoro-5-p-chlorophenyl-7-nitro-2,3-dihydro-1H-1,4-benzodiazepin-2-one.
91. 1-Methyl-3-fluoro-5-o-bromophenyl-7-nitro-2,3-dihydro-1H-1,4-benzodiazepin-2-one.
92. 1-Methyl-3-fluoro-5-m-bromophenyl-7-nitro-2,3-dihydro-1H-1,4-benzodiazepin-2-one.
93. 1-Methyl-3-fluoro-5-p-bromophenyl-7-nitro-2,3-dihydro-1H-1,4-benzodiazepin-2-one.
94. 1-Methyl-3-fluoro-5-(2-pyridyl)-7-nitro-2,3-dihydro-1H-1,4-benzodiazepin-2-one.
95. 1-Methyl-3-fluoro-5-(3-pyridyl)-7-nitro-2,3-dihydro-1H-1,4-benzodiazepin-2-one.
96. 1-Methyl-3-fluoro-5-(4-pyridyl)-7-nitro-2,3-dihydro-1H-1,4-benzodiazepin-2-one.

EXAMPLES 97–122

The following are obtained by the procedure of Example 71 from the corresponding 3,7-dibromo compounds:

97. 3-Fluoro-5-phenyl-7-bromo-2,3-dihydro-1H-1,4-benzodiazepin-2-one.
98. 3-Fluoro-5-o-fluorophenyl-7-bromo-2,3-dihydro-1H-1,4-benzodiazepin-2-one.
99. 3-Fluoro-5-m-fluorophenyl-7-bromo-2,3-dihydro-1H-1,4-benzodiazepin-2-one.
100. 3-Fluoro-5-p-fluorophenyl-7-bromo-2,3-dihydro-1H-1,4-benzodiazepin-2-one.
101. 3-Fluoro-5-o-chlorophenyl-7-bromo-2,3-dihydro-1H-1,4-benzodiazepin-2-one.
102. 3-Fluoro-5-m-chlorophenyl-7-bromo-2,3-dihydro-1H-1,4-benzodiazepin-2-one.
103. 3-Fluoro-5-p-chlorphenyl-7-bromo-2,3-dihydro-1H-1,4-benzodiazepin-2-one.
104. 3-Fluoro-5-o-bromophenyl-7-bromo-2,3-dihydro-1H-1,4-benzodiazepin-2-One.
105. 3-Fluoro-5-m-bromophenyl-7-bromo-2,3-dihydro-1H-1,4-benzodiazepin-2-one.
106. 3-Fluoro-5-p-bromophenyl-7-bromo-2,3-dihydro-1H-1,4-benzodiazepin-2-one.
107. 3-Fluoro-5-(2-pyridyl)-7-bromo-2,3-dihydro-1H-1,4-benzodiazepin-2-one.
108. 3-Fluoro-5-(3-pyridyl)-7-bromo-2,3-dihydro-1H-1,4-benzodiazepin-2-one.
109. 3-Fluoro-5-(4-pyridyl)-7-bromo-2,3-dihydro-1H-1,4-benzodiazepin-2-one.
110. 1-Methyl-3-fluoro-5-phenyl-7-bromo-2,3-dihydro-1H-1,4-benzodiazepin-2-one.
111. 1-Methyl-3-fluoro-5-o-fluorophenyl-7-bromo-2,3-dihydro-1H-1,4-benzodiazepin-2-one.
112. 1-Methyl-3-fluoro-5-m-fluorophenyl-7-bromo-2,3-dihydro-1H-1,4-benzodiazepin-2-one.
113. 1-Methyl-3-fluoro-5-p-fluorophenyl-7-bromo-2,3-dihydro-1H-1,4-benzodiazepin-2-one.
114. 1-Methyl-3-fluoro-5-o-chlorophenyl-7-bromo-2,3-dihydro-1H-1,4-benzodiazepin-2-one.
115. 1-Methyl-3-fluoro-5-m-chlorophenyl-7-bromo-2,31-dihydro-1H-1,4-benzodiazepin-2-one.
116. 1-Methyl-3-fluoro-5-p-chlorophenyl-7-bromo-2,3-dihydro-1H-1,4-benzodiazepin-2-one.
117. 1-Methyl-3-fluoro-5-o-bromophenyl-7-bromo-2,3-dihydro-1H-1,4-benzodiazepin-2-one.
118. 1-Methyl-3-fluoro-5-m-bromophenyl-7-bromo-2,3-dihydro-1H-1,4-benzodiazepin-2-one.
119. 1-Methyl-3-fluoro-5-p-bromophenyl-7-bromo-2,3-dihydro-1H-1,4-benzodiazepin-2-one.
120. 1-Methyl-3-fluoro-5-(2-pyridyl)-7-bromo-2,3-dihydro-1H-1,4-benzodiazepin-2-one.
121. 1-Methyl-3-fluoro-5-(3-pyridyl)-7-bromo-2,3-dihydro-1H-1,4-benzodiazepin-2-one.
122. 1-Methyl-3-fluoro-5-(4-pyridyl)-7-bromo-2,3-dihydro-1H-1,4-benzodiazepin-2-one.

EXAMPLE 123

3.42 g. of 3,7-dichloro-5-o-chlorophenyl-2,3-dihydro-1H-1,4-benzodiazepin-2-one are dissolved in 50 ml. of anhydrous HF and 0.5 g. of $SbCl_5$ is added. After heating under reflux for one day, with stirring, the mixture is worked up in the customary manner using sodium carbonate solution and methylene chloride. This gives 3-fluoro-5-o-chlorophenyl-7-chloro-2,3-dihydro-1H-1,4-benzodiazepin-2-one, m.p. 220° (decomposition).

EXAMPLE 124

A mixture of 3.42 g. of 3,7-dichloro-5-o-chlorophenyl-2,3-dihydro-1H-1,4-benzodiazepin-2-one, 7.2 g. of $SbF_3$ and 0.5 g. of $SbF_5$ is heated at its melting point for 1.5 hours. After cooling, the mixture is worked up by the method of Example 11 to give 3-fluoro-5-o-chlorophenyl-7-chloro-2,3-dihydro-1H-1,4-benzodiazepin-2-one, m.p. 220° (decomposition).

EXAMPLE 125

2.2 g. of N-bromosuccinimide are added at 20°, with stirring, to a suspension of 2.85 g. of diazepam in 50 ml. of $CCl_4$. The mixture is heated under reflux for one hour; a further 1.1 g. of N-bromosuccinimide are added and the mixture is heated for 30 minutes more. The mixture is concentrated; the succinimide formed is filtered off; the filtrate is evaporated and treated with 50 ml. of acetonitrile; 3.9 g. of AgF are added to the resulting solution; which contains 3-bromodiazepam. After stirring for 3 hours at 20° and standing overnight, the mixture is filtered through active charcoal, evaporated and worked up in the customary manner using sodium bicarbonate solution/ethyl acetate. This gives 3-fluorodiazepam. m.p. 152°–154°.

EXAMPLE 126

3 g. of 3-aminodiazepam are dissolved in a mixture of 140 g. of HF and 60 ml. of absolute pyridine at 20° and 1.05 g. of $NaNO_2$ are added. After stirring for 1 hour, the mixture is worked up in the customary manner using ice water and methylene chloride. This gives 3-fluorodiazepam, m.p. 152°–154°.

EXAMPLE 127

3 g. of 3-aminodiazepam are dissolved in 30 ml. of hydrogen fluoride and an equivalent amount of isoamyl nitrite is added dropwise at 0° to the stirred mixture. After stirring for 2 hours more, the mixture is poured into sodium carbonate solution at 0° and worked up in the customary manner to give 3-fluorodiazepam, m.p. 152°–154°.

EXAMPLE 128

A solution of 5.5 g. of $Tl(CF_3COO)_3$ in 100 ml. of acetonitrile is added to a solution of 2.85 g. of Diazepam in 50 ml. of acetonitrile, in the dark and at 20°, and the mixture is stirred for 20 hours at 20°. The solution is concentrated and precipitated benzodiazepin-2-one-3-yl thallium-bis(trifluoroacetate) is filtered off, washed several times with ether and dissolved in a minimum amount of acetonitrile. 1.2 g. of KF are added to the stirred solution at 40°. After stirring for 5 hours more, the mixture is evaporated and the resulting benzodiazepin-3-on-3-yl thallium difluoride is suspended in 100 ml. of THF; 1 ml. of BF$_3$-etherate is added to the suspension and the mixture is stirred for 2 hours at 20° and worked up in the customary manner to give 3-fluorodiazepam, m.p. 152°–154°.

EXAMPLE 129

2.85 g. of Diazepam are dissolved in 100 ml. of anhydrous HF and the solution is electrolyzed using a direct current of 50 amperes and a voltage of 5.2 volts at 5°. The reaction mixture is poured into ice cold sodium carbonate solution and worked up in the customary manner. This gives 3-fluorodiazepam, m.p. 152°–154°.

EXAMPLE 130

A solution of phenylmagnesium bromide is prepared from 7.85 g. of bromobenzene and 1.25 g. of Mg in 100 ml. of THF and a solution of 2.61 g. of 1-methyl-3-fluoro-5,7-dichloro-2,3-dihydro-1H-1,4-benzodiazepin-2-one, obtainable by addition of HF to 1-methyl-2,5-dihydro-1H-1,4-benzodiazepin-2,5-dione to give the 3-fluoro derivative and reaction with PCl$_5$, in 150 ml. of THF is added dropwise at about 20° to the stirred mixture. After 2 hours heating under reflux and stirring, the mixture is cooled, diluted with 100 ml. of ether and decomposed by ammonium chloride solution. Working up in the customary manner gives 3-fluorodiazepam, m.p. 152°–154°.

EXAMPLE 131

A solution of 2.71 g. of 1-methyl-3-fluoro-5-ethoxy-7-chloro-2,3-dihydro-1H-1,4-benzodiazepin-2-one in 20 ml. of di-n-butyl ether is added, under N$_2$ at 130°, to a solution of 1.25 g. of phenyl lithium in 30 ml. of di-n-butyl ether. The mixture is heated under reflux for 6 hours, cooled and worked up in the customary manner using NH$_4$Cl solution/CHCl$_3$ to give 3-fluorodiazepam, m.p. 152°–154°.

EXAMPLE 132

3.57 g. of 1-(2,2,2-trifluoroethyl)-3-fluoro-5-phenyl-7-chloro-2,3-dihydro-1H-1,4-benzodiazepine, obtainable from the corresponding 3-hydroxy compound by reaction with SOCl$_2$ and then AgF, is dissolved in a mixture of 35 ml. of acetone and 20 ml. of pyridine; 1.35 g. of KMnO$_4$ are added in portions. During the addition, the mixture is briefly boiled up after each addition until the violet color has disappeared. The mixture is then heated at 100° for 1 hour more. NaHSO$_3$ solution is added to decompose the excess oxidizing agent and the mixture is worked up in the customary manner to give 1-(2,2,2-trifluoroethyl)-3-fluoro-5-phenyl-7-chloro-2,3-dihydro-1H-1,4-benzodiazepin-2-one.

EXAMPLE 133

A solution of 2.91 g. of 2-hydroxy-3-fluoro-5-phenyl-7-chloro-2,3-dihydro-1H-1,4-benzodiazepine, obtainable from 2-amino-5-chloro-benzophenone-N-(2,2-diethoxy-1-fluoroethyl)imine and HF, in 250 ml. of absoute pyridine is added dropwise to a solution of 2 g. of CrO$_3$ in 15 ml. of absolute pyridine. After one hour's stirring at about 20°, the mixture is stirred into ice water and worked up in the customary manner using ethyl acetate. This gives 3-fluoro-5-phenyl-7-chloro-2,3-dihydro-1H-1,4-benzodiazepin-2-one, m.p. 235° (decomposition).

EXAMPLE 134

3.19 g. of 3-fluoro-diazepam-N-oxide, obtainable from 2-(α-fluoro-α-iodo-N-methyl-acetamido)-5-chloro-benzophenone oxime and pyridine, is heated under reflux for 30 minutes with a mixture of 40 ml. of absolute benzene and 20 ml. of SOCl$_2$. Excess SOCl$_2$ is then removed by repeatedly distilling it off and adding benzene. The residue is taken up in DMF and is stirred into sodium carbonate solution at 0°. The product is filtered off and is washed with sodium carbonate solution, water, isopropanol and ether to give 3-fluorodiazepam, m.p. 152°–154°.

EXAMPLE 135

3.19 g. of 3-fluorodiazepam-N-oxide are boiled for 2 hours with 16 ml. of triethyl phosphite in 100 ml. of dioxane and the mixture is evaporated and worked up in the customary manner to give 3-fluorodiazepam, m.p. 152°–154°.

EXAMPLE 136

2.35 g. of sublimed potassium tert.-butylate are added at 5° to a solution of 4.55 g. of 3-fluoro-4-p-toluenesulfonyl-5-phenyl-7-nitro-2,3,4,5-tetrahydro-1H-1,4-benzodiazepin-2-one, obtainable from 4-p-toluenesulfonyl-5-phenyl-7-nitro-2,3,4,5-tetrahydro-1H-1,4-benzodiazepin-2-one and CF$_3$OF, in 50 ml. of DMF. After stirring for 1 hour, the temperature is allowed to rise to 20° and the mixture is stirred for 48 hours more. The mixture is poured onto ice and worked up in the customary manner to give 3-fluoro-5-phenyl-7-nitro-2,3-dihydro-1H-1,4-benzodiazepin-2-one.

EXAMPLE 137

4.5 ml. of POCl$_3$ are added to a solution of 3.19 g. of 1-methyl-3-fluoro-4-hydroxy-5-phenyl-7-chloro-2,3,4,5-tetrahydro-1H-1,4-benzodiazepin-2-one, obtainable from N-[2-(α-fluoro-α-iodo-N-methylacetamido)-5-chloro-benzhydryl]-hydroxylamine and 1,4-diazabicyclo[4,3,0]-non-5-ene, in 100 ml. of CH$_2$Cl$_2$ and the mixture is stirred for 3 hours at 20°. The mixture is evaporated; excess POCl$_3$ is removed by distillation with benzene; the residue is taken up in DMF and is stirred into sodium carbonate solution at 0°. The resulting precipitate is filtered off. The product is 1-methyl-3-fluoro-5-phenyl-7-chloro-2,3-dihydro-1H-1,4-benzodiazepin-2-one, m.p. 152°–154°.

EXAMPLE 138

3.47 g. of 5-fluoro-7-methyl-10-chloro-11b-phenyl-2,3,5,6,7,11b-hexahydro-oxazolo[3,2-d]-1,4-benzodiazepin-6-one, obtainable from 2-(α-bromo-α-fluoro-N-methyl-acetamido)-5-chlorobenzophenone and 2-aminoethanol, and 1 g. of sodium acetate are heated under reflux for 2 hours with 10 ml. of acetic anhydride. The mixture is cooled, poured onto ice and worked up in the customary manner to give 3-fluorodiazepam, m.p. 152°–154°.

EXAMPLE 139

3.7 g. of 3-fluoro-5-o-chlorophenyl-7-chloro-2,3-dihydro-1H-1,4-benzodiazepin-2-one-3-carboxylic acid, obtainable from 5-o-chlorophenyl-7-chloro-2,3-dihydro-1H-1,4-benzodiazepin-2-one-3-carboxylic acid and CF$_3$OF, in 50 ml. of pyridine are boiled for 1 hour with 0.5 g. of CuO. The mixture is cooled, poured onto ice and filtered to give 3-fluoro-5-o-chlorophenyl-7-chloro- 2,3-dihydro-1H-1,4-benzodiazepin-2-one, m.p. 211° (decomposition).

EXAMPLE 140

A mixture of 4.03 g. of 3-fluorodiazepam-3-carboxylic acid tert.-butyl ester and 100 mg. of p-toluenesulfonic acid is warmed to 140°–145° for 20 minutes. The mixture is cooled and worked up in the customary manner to give 3-fluorodiazepam, m.p. 152°–154°.

EXAMPLE 141

3.3 g of 3-fluorocarbonyloxy-5-phenyl-7-chloro-2,3-dihydro-1H-1,4-benzodiazepin-2-one, obtainable from the 3-hydroxy compound and FCOOCH$_3$, is warmed to 60° with 20 ml. of pyridine for 20 minutes. The mixture is then poured into ice water and worked up in the customary manner. The product is 3-fluoro-5-phenyl-7-chloro-2,3-dihydro-1H-1,4-benzodiazepin-2-one, m.p. 235° (decomposition).

EXAMPLE 142

2.1 g. of p-toluenesulfochloride are added to a solution of 3.21 g. of 2-(N-methylfluoroacetamido)-5-chlorobenzophenone oxime, obtainable from 2-methylamino-5-chlorobenzophenone oxime and fluoroacetyl chloride, in 30 ml. of pyridine and the mixture is warmed for 1 hour at 80°. Working up in the customary manner gives 3-fluorodiazepam, m.p. 152°–154°.

EXAMPLE 143

1.25 g. of 1,4-diazabicyclo[4,3,0]-non-5-ene are added to a solution of 4.75 g. of O-p-toluenesulfonyl-2-(N-methylfluoroacetamido)-5-chlorobenzophenone oxime in 20 ml. of DMSO and the mixture is stirred for one hour at 5°–10°. The mixture is poured onto ice and worked up in the customary manner to give 3-fluorodiazapam, m.p. 152°–154°.

EXAMPLE 144

25 ml. of 0.5 N sodium hydroxide solution are added to a solution of 2.45 g. of 2-methylamino-5-chlorobenzophenone imine in 25 ml. of benzene, stirred at 0°–5°. A solution of 2.5 g. of α-fluoro-α-bromoacetyl bromide in 5 ml. of benzene is then added, the mixture is vigorously stirred for 15 minutes, 11.5 ml. of 1 N sodium hydroxide solution are added and the mixture is stirred for 2 hours more. Working up in the customary manner gives 3-fluorodiazepam, m.p. 152°–154°.

EXAMPLE 145

4.97 g. of 2-(2-α-bromo-α-fluoroacetamido-5-bromobenzoyl)-pyridine hydrobromide, obtainable from 2-(2-amino-5-bromobenzoylpyridine and α-bromo-α-fluoroacetyl bromide, and 3.12 g. of hexamethylenetetramine in 75 ml. of methanol are heated under reflux for 10 hours. 2-(2-α-Amino-α-fluoroacetamido-5-bromo-benzoyl)-pyridine is formed an an intermediate. The mixture is evaporated and worked up in the customary manner to give 3-fluoro-5-(2-pyridyl)-7-bromo-2,3-dihydro-1H-1,4-benzodiazepin-2-one.

EXAMPLE 146

NH$_3$ is passed into a refluxing solution of 1.48 g. of hexamethylenetetramine in 30 ml. of ethanol; 3.83 g. of 2-(α-bromo-α-fluoroacetamido)-5-nitro-2'-fluorobenzophenone, obtainable from 2-amino-5-nitro-2'-fluorobenzophenone and α-bromo-α-fluoroacetyl bromide, are added over 2 hours. The mixture is then heated under reflux for 3 hours more and is evaporated. The resulting 2-(α-amino-α-fluoroacetamido)-5-nitro-2'-fluorobenzophenone is treated with 15 ml. of toluene and 20 mg. of p-toluenesulfonic acid and is heated under reflux for 1 hour. Working up in the customary manner gives 3-fluoro-5-o-fluorophenyl-7-nitro-2,3-dihydro-1H-1,4-benzodiazepin-2-one.

EXAMPLE 147

A solution of 3.40 g. of 2-(α-chloro-α-fluoro-N-methyl-acetamido)-5-chlorobenzophenone, obtainable from 2-methylamino-5-chlorobenzophenone and α-chloro-α-fluoroacetyl chloride, and 3.4 g. of hexamethylenetetramine in 50 ml. of ethanol is heated under reflux for 10 hours and is evaporated. The mixture is worked up in the customary manner, using water and benzene, to give 3-fluorodiazepam, m.p. 152°–154°.

EXAMPLE 148

3.65 g. of 2-(α-bromo-α-fluoro-N-methylacetamido)-5-chlorobenzophenone, obtainable from 2-methylamino-5-chlorobenzophenone and α-bromo-α-fluoroacetyl bromide, and 3.5 g. of dinitrosopentamethylenetetramine in 70 ml. of ethanol are heated under reflux for 9 hours. The mixture is evaporated and worked up in the customary manner, using ether and water, to give 3-fluorodiazepam, m.p. 152°–154°.

EXAMPLE 149

A solution of 3.71 g. of 2-(α-bromo-α-fluoroacetamido)-5-chlorobenzophenone, obtainable from 2-amino-5-chlorobenzophenone and α-bromo-α-fluoroacetyl bromide, in 100 ml. of ether and 60 ml. of 13% methanolic NH$_3$ is allowed to stand for 18 hours at 20° and is evaporated. Working up in the customary manner, using water/methylene chloride, gives 3-fluoro-5-phenyl-7-chloro-2,3-dihydro-1H-1,4-benzodiazepin-2-one.

EXAMPLE 150

NH$_3$ is passed into a solution of 3.26 g. of 2-(α-chloro-α-fluoro-acetamido)-5-chloro-benzophenone, obtainable from 2-amino-5-chlorobenzophenone and α-chloro-α-fluoroacetyl chloride, in 15 ml. of DMSO at 50° for one hour. After stirring for 16 hours, the mixture is evaporated; 35 ml. of chloroform and 35 ml. of 13% NHO$_3$ are added and the resulting salt is filtered off. The product is suspended in ethanol and neutralized with ammonia. Dilution with water gives 3-fluoro-5-phenyl-7-chloro-2,3-dihydro-1H-1,4-benzodiazepin-2-one, m.p. 235° (decomposition).

EXAMPLE 151

15 ml. of liquid NH$_3$ are added at −30° to a solution of 3.26 g. of 2-(α-chloro-α-fluoroacetamido)-5-chlorobenzophenone in 35 ml. of DMF and the mixture is maintained at −30° for 5 hours. The mixture is evaporated and worked up in the customary manner to give 3-fluoro-5-phenyl-7-chloro-2,3-dinydro-1H-1,4-benzodiazepin-2-one, m.p. 235° (decomposition).

EXAMPLE 152

50 ml. of liquid NH$_3$ are added to a solution of 3.85 g. of 2-(α-bromo-α-fluoro-N-methyl-acetamido)-5-chlorobenzophenone in 50 ml. of methylene chloride and the solution is then stirred for 5 hours, the ammonia being kept under reflux by means of a solid carbon dioxide condenser. The mixture is evaporated and worked up in the customary manner to give 3-fluorodiazepam, m.p. 152°–154°.

EXAMPLE 153

A solution of 3.07 g. of 2-(α-amino-α-fluoroacetamido)-5-chlorobenzophenone, obtainable from 2-(α-bromo-α-fluoroacetamido)-5-chlorobenzophenone and liquid NH$_3$, in 35 ml. of pyridine is boiled for 2 hours and evaporated. Working up in the customary manner gives 3-fluoro-5-phenyl-7-chloro-2,3-dihydro-1H-1,4-benzodiazepin-2-one, m.p. 235° (decomposition).

EXAMPLE 154

A mixture of 4.37 g. of 2-(α-fluoro-α-phthalimidoacetamido)-5-chlorobenzophenone, obtainable from 2-(α-chloro-α-fluoro-acetamido)-5-chlorobenzophenone and potassium phthalimide, 1.5 g. of hydrazine hydrate and 70 ml. of methanol is heated under reflux for 2 hours, evaporated and worked up in the customary manner. This gives 3-fluoro-5-phenyl-7-chloro-2,3-dihydro-1H-1,4-benzodiazepin-2-one, m.p. 235° (decomposition).

EXAMPLE 155

A solution of 3.13 g. of hydrazine hydrate in 100 ml. of ethanol is added to a stirred suspension of 34.7 g. of 2-(α-azido-α-fluoro-N-methyl-acetamido)-5-chlorobenzophenone, obtainable from 2-(α-chloro-α-fluoro-N-methyl-acetamido)-5-chlorobenzophenone and NaN$_3$, and 2 g. of 5% palladium-on-charcoal catalyst in 300 ml. of ethanol at 20°. The mixture is stirred for an hour more at 40°; nitrogen is evolved; the product is filtered, evaporated and worked up in the customary manner to give 3-fluorodiazepam, m.p. 152°–154°.

EXAMPLE 156

Hydrogen is passed into a solution of 3.33 g. of 2-(α-azido-α-fluoro-acetamido)-5-chlorobenzophenone in 100 ml. of ethyl acetate in the presence of 0.3 g. of 5% palladium-on-charcoal for 4 hours. After filtering off the catalyst, evaporation and working up in the customary manner, there is obtained 3-fluoro-5-phenyl-7-chloro-2,3-dihydro-1H-1,4-benzodiazepin-2-one, m.p. 235° (decomposition).

EXAMPLE 157

3.45 g. of α-fluoro-α-(2-amino-5-nitrobenzhydrylideneamino)-acetic acid ethyl ester, obtainable by reacting 2-amino-5-nitro-benzophenone with α-fluoro-α-bromo-orthoacetic acid triethyl ester to give 2-(1-ethoxy-2-fluoro-2-bromo-ethylideneamino)-5-nitrobenzophenone and rearrangement by means of liquid NH$_3$ in CH$_2$Cl$_2$, is heated with 2.5 g. of 2-methylimidazole for 45 minutes at 140° and the mixture is cooled and worked up in the customary manner, using water/ethyl acetate, to give 3-fluoro-5-phenyl-7-nitro-2,3-dihydro-1H-1,4-benzodiazepin-2-one, m.p. 218° (decomposition).

EXAMPLE 158

A mixture of 3.28 g. of N-methyl-p-chloro-α-fluoro-α-iodoacetanilide, obtainable by reacting p-chloro-N-methylaniline with α-chloro-α-fluoroacetyl chloride and treating the product with NaI, 0.8 g. of benzonitrile and 3 ml. of SnCl$_4$ is heated under reflux for 2 hours.

The mixture is then worked up in the customary manner, using dilute sodium hydroxide solution/methylene chloride, to give 3-fluorodiazepam, m.p. 152°–154°.

EXAMPLE 159

0.15 g. of anhydrous FeCl$_3$ and 2.53 g. of 3-fluoro-5-phenyl-2,3-dihydro-1H-1,4-benzodiazepin-2-one, obtainable from 3-chloro-5-phenyl-2,3-dihydro-1H-1,4-benzodiazepin-2-one and AgF, are added at 10° to a solution of 1 g. of chlorine in 25 ml. of dry nitrobenzene. The mixture is stirred in the dark for 30 hours at 20° and is worked up in the customary manner. The product is 3-fluoro-5-phenyl-7-chloro-2,3-dihydro-1H-1,4-benzodiazepin-2-one, m.p. 235° (decomposition).

EXAMPLE 160

The calculated quantity of chlorine is passed into a solution of 2.53 g. of 3-fluoro-5-phenyl-2,3-dihydro-1H-1,4-benzodiazepin-2-one in 25 ml. of nitrobenzene. The hydrogen chloride formed is then removed, first by an air stream and then under reduced pressure. The mixture is evaporated and worked up in the customary manner, using sodium carbonate solution/methylene chloride, to give 3-fluoro-5-phenyl-7-chloro-2,3-dihydro-1H-1,4-benzodiazepin-2-one, m.p. 235° (decomposition).

EXAMPLE 161

2.67 g. of 1-methyl-3-fluoro-5-phenyl-2,3-dihydro-1H-1,4-benzodiazepin-2-one, obtainable from the corresponding 3-chloro compound and AgF, is heated under reflux for one hour with 10 ml. of freshly distilled SO$_2$Cl$_2$ and a mixture of 6 g. of SO$_2$Cl$_2$, 0.1 g. of S$_2$Cl$_2$ and 0.1 g. of AlCl$_3$ is added. After one hour, the mixture is evaporated. The remainder of the SO$_2$Cl$_2$ is removed by repeated distillation with benzene and the mixture is worked up in the customary manner. The product is 3-fluorodiazepam, m.p. 152°–154°.

EXAMPLE 162

1.6 g. of bromine in 10 ml. of CCl$_4$ are added dropwise, over the course of 4 hours, to a refluxing stirred solution of 2.53 g. of 1-methyl-3-fluoro-5-phenyl-2,3-dihydro-1H-1,4-benzodiazepin-2-one in 100 ml. of CCl$_4$. The mixture is boiled for 2 hours more; the HBr formed is removed by means of N$_2$ and the mixture is evaporated and worked up in the customary manner to give 1-methyl-3-fluoro-5-phenyl-7-bromo-2,3-dihydro-1H-1,4-benzodiazepin-2-one.

EXAMPLE 163

1.2 g. of acetyl nitrate are added dropwise, at 10° to a stirred solution of 2.67 g. of 1-methyl-3-fluoro-5-phenyl-2,3-dihydro-1H-1,4-benzodiazepin-2-one in 70 ml. of CCl$_4$ and 20 ml. of acetonitrile. The mixture is stirred for 1 hour more at 10° and for 3 hours at 20° and is poured into ice cold sodium carbonate solution and worked up in the customary manner to give 1-methyl-3-fluoro-5-phenyl-7-nitro-2,3-dihydro-1H-1,4-benzodiazapin-2-one.

EXAMPLE 164

A solution of 0.8 g. of NO$_2$F in 13 ml. of sulfolane is saturated with BF$_3$ at 5°–10°. This solution is added dropwise to a stirred solution of 3.03 g. of 1-methyl-3-fluoro-5-o-chlorophenyl-2,3-dihydro-1H-1,4-benzodiazepin-2-one, obtainable from the corresponding 3-chloro compound and AgF, in 15 ml. of sulfolane at 10°–15°. The mixture is stirred for 1 hour more at 15°–25° and worked up in the customary manner to give 1-methyl-3-fluoro-5-o-chlorophenyl-7-nitro-2,3-dihydro-1H-1,4-benzodiazepin-2-one.

EXAMPLES 165–177

By following the method of Example 71, the following compounds are obtained from the corresponding 3-chloro compounds:

165. 3,7-Difluoro-5-phenyl-2,3-dihydro-1H-1,4-benzodiazepin-2-one.
166. 3,7-Difluoro-5-o-fluorophenyl-2,3-dihydro-1H-1,4-benzodiazepin-2-one.
167. 3,7-Difluoro-5-m-fluorophenyl-2,3-dihydro-1H-1,4-benzodiazepin-2-one.
168. 3,7-Difluoro-5-p-fluorophenyl-2,3-dihydro-1H-1,4-benzodiazepin-2-one.
169. 3,7-Difluoro-5-o-chlorophenyl-2,3-dihydro-1H-1,4-benzodiazepin-2-one, m.p. 213°–215°.
170. 3,7-Difluoro-5-m-chlorophenyl-2,3-dihydro-1H-1,4-benzodiazepin-2-one.
171. 3,7-Difluoro-5-p-chlorophenyl-2,3-dihydro-1H-1,4-benzodiazepin-2-one.
172. 3,7-Difluoro-5-o-bromophenyl-2,3-dihydro-1H-1,4-benzodiazepin-2-one.
173. 3,7-Difluoro-5-m-bromophenyl-2,3-dihydro-1H-1,4-benzodiazepin-2-one.
174. 3,7-Difluoro-5-p-bromophenyl-2,3-dihydro-1H-1,4-benzodiazepin-2-one.
175. 3,7-Difluoro-5-(2-pyridyl)-2,3-dihydro-1H-1,4-benzodiazepin-2-one.
176. 3,7-Difluoro-5-(3-pyridyl)-2,3-dihydro-1H-1,4-benzodiazepin-2-one.
177. 3,7-Difluoro-5-(4-pyridyl)-2,3-dihydro-1H-1,4-benzodiazepin-2-one.

EXAMPLES 178–190

By the procedure given in Example 125, the following are obtained from the corresponding compounds unsubstituted in 3-position, treated with N-bromosuccinimide and then AgF:

178. 1-Methyl-3,7-difluoro-5-phenyl-2,3-dihydro-1H-1,4-benzodiazepin-2-one.
179. 1-Methyl-3,7-difluoro-5-o-fluorophenyl-2,3-dihydro-1H-1,4-benzodiazepin-2-one.
180. 1-Methyl-3,7-difluoro-5-m-fluorophenyl-2,3-dihydro-1H-1,4-benzodiazepin-2-one.
181. 1-Methyl-3,7-difluoro-5-p-fluorophenyl-2,3-dihydro-1H-1,4-benzodiazepin-2-one.
182. 1-Methyl-3,7-difluoro-5-o-chlorophenyl-2,3-dihydro-1H-1,4-benzodiazepin-2-one, m.p. 230°–232°.
183. 1-Methyl-3,7-difluoro-5-m-chlorophenyl-2,3-dihydro-1H-1,4-benzodiazepin-2-one.
184. 1-Methyl-3,7-difluoro-5-p-chlorophenyl-2,3-dihydro-1H-1,4-benzodiazepin-2-one.
185. 1-Methyl-3,7-difluoro-5-o-bromophenyl-2,3-dihydro-1H-1,4-benzodiazepin-2-one.
186. 1-Methyl-3,7-difluoro-5-m-bromophenyl-2,3-dihydro-1H-1,4-benzodiazepin-2-one.
187. 1-Methyl-3,7-difluoro-5-p-bromophenyl-2,3-dihydro-1H-1,4-benzodiazepin-2-one.
188. 1-Methyl-3,7-difluoro-5-(2-pyridyl)-2,3-dihydro-1H-1,4-benzodiazepin-2-one.
189. 1-Methyl-3,7-difluoro-5-(3-pyridyl)-2,3-dihydro-1H-1,4-benzodiazepin-2-one.
190. 1-Methyl-3,7-difluoro-5-(4-pyridyl)-2,3-dihydro-1H-1,4-benzodiazepin-2-one.

The examples which follow relate to pharmaceutical preparations containing the compounds of Formula I or their acid addition salts:

EXAMPLE A: Tablets

A mixture of 1 kg. of 3-fluorodiazepam, 4 kg. of lactose, 1.2 kg. of potato starch, 0.2 kg. of talc and 0.1 kg. of magnesium stearate is pressed into tablets in the customary manner in such a way that each tablet contains 10 mg. of active compound.

EXAMPLE B: Dragees

Tablets are pressed according to Example A and are coated in the customary manner with a coating composed of sucrose, potato starch, talc, tragacanth and dyestuff.

EXAMPLE C: Capsules

Hard gelatine capsules are filled with 5 kg. of 3-fluorodiazepam in the customary manner in such a way that each capsule contains 5 mg. of active compound.

Tablets, dragees and capsules containing one or more of the remaining active compounds of Formula I and/or their physiologically acceptable acid addition salts, can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 3-fluorobenzodiazepine of the formula

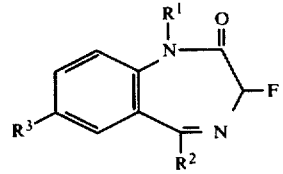

wherein $R^1$ is H, alkyl or fluorinated alkyl of 1–4 carbon atoms and up to 9 fluorine atoms or cycloalkylalkyl of 4–8 carbon atoms; $R^2$ is phenyl, monohalophenyl or pyridyl; $R^3$ is F, Cl, Br or $NO_2$, and physiologically acceptable acid addition salts thereof.

2. A compound of claim 1, wherein $R^1$ is H, methyl, ethyl, 2,2,2-trifluoroethyl or cyclopropylmethyl.

3. A compound of claim 1, wherein $R^2$ is phenyl, o-fluorophenyl, o-chlorophenyl or 2-pyridyl.

4. A compound of claim 1, wherein $R^3$ is F, Cl or $NO_2$.

5. A compound of claim 1, wherein $R^1$ is H, methyl, ethyl, 2,2,2-trifluoroethyl or cyclopropylmethyl and $R^2$ is phenyl, o-fluorophenyl, o-chlorophenyl or 2-pyridyl.

6. A compound of claim 1, wherein $R^1$ is H, methyl or ethyl and $R^2$ is phenyl, o-fluorophenyl, o-chlorophenyl or 2-pyridyl.

7. A compound of claim 1, wherein $R^1$ is H or methyl and $R^2$ is phenyl, o-fluorophenyl, o-chlorophenyl or 2-pyridyl.

8. A compound of claim 1, wherein $R^1$ is H or methyl, $R^2$ is phenyl, o-fluorophenyl or o-chlorophenyl and $R^3$ is F, Cl or $NO_2$.

9. A compound of claim 1, wherein $R^1$ is H or methyl and $R^2$ is phenyl or o-chlorophenyl.

10. A compound of claim 1, wherein $R^1$ is H and $R^2$ is phenyl, o-fluorophenyl, o-chlorophenyl or 2-pyridyl.

11. A compound of claim 1, wherein $R^1$ is H or methyl, $R^2$ is phenyl or o-chlorophenyl and $R^3$ is F, Cl or $NO_2$.

12. A compound of claim 1, wherein $R^1$ is H or methyl, $R^2$ is phenyl or o-chlorophenyl and $R^3$ is F or Cl.

13. 3-Fluoro-5-phenyl-7-chloro-2,3-dihydro-1H-1,4-benzodiazepin-2-one, a compound of claim 1.

14. 1-Methyl-3-fluoro-5-phenyl-7-chloro-2,3-dihydro-1H-1,4-benzodiazepin-2-one, a compound of claim 1.

15. 1-(2,2,2-Trifluoroethyl)-3-fluoro-5-phenyl-7-chloro-2,3-dihydro-1H-1,4-benzodiazepin-2-one, a compound of claim 1.

16. 1-Cyclopropylmethyl-3-fluoro-5-phenyl-7-chloro-2,3-dihydro-1H-1,4-benzodiazepin-2-one, a compound of claim 1.

17. 3-Fluoro-5-o-chlorophenyl-7-chloro-2,3-dihydro-1H-1,4-benzodiazepin-2-one, a compound of claim 1.

18. 1-Methyl-3-fluoro-5-o-chlorophenyl-7-chloro-2,3-dihydro-1H-1,4-benzodiazepin-2-one, a compound of claim 1.

19. 3-Fluoro-5-(2-pyridyl)-7-bromo-2,3-dihydro-1H-1,4-benzodiazepin-2-one, a compound of claim 1.

20. 1-Methyl-3-fluoro-5-(2-pyridyl)-7-bromo-2,3-dihydro-1H-1,4-benzodiazepin-2-one, a compound of claim 1.

21. 3-Fluoro-5-phenyl-7-nitro-2,3-dihydro-1H-1,4-benzodiazepin-2-one, a compound of claim 1.

22. 3-Fluoro-5-o-fluorophenyl-7-nitro-2,3-dihydro-1H-1,4-benzodiazepin-2-one, a compound of claim 1.

23. 1-Methyl-3-fluoro-5-o-fluorophenyl-7-nitro-2,3-dihydro-1H-1,4-benzodiazepin-2-one, a compound of claim 1.

24. 3-Fluoro-5-o-chlorophenyl-7-nitro-2,3-dihydro-1H-1,4-benzodiazepin-2-one, a compound of claim 1.

25. 1-Methyl-3-fluoro-5-o-chlorophenyl-7-nitro-2,3-dihydro-1H-1,4-benzodiazepin-2-one, a compound of claim 1.

26. 3,7-Difluoro-5-o-chlorophenyl-2,3-dihydro-1H-1,4-benzodiazepin-2-one, a compound of claim 1.

27. 1-Methyl-3,7-difluoro-5-o-chlorophenyl-2,3-dihydro-1H-1,4-benzodiazepin-2-one, a compound of claim 1.

28. A pharmaceutical composition in unit dosage form comprising a central nervous system depressant effective amount per unit dosage of a compound of claim 1, in admixture with a pharmaceutically acceptable carrier.

29. A method of depressing central nervous system activity in mammals comprising administering to a patient a daily dosage of a compound of claim 1, in admixture with a pharmaceutically acceptable carrier, effective to induce a muscle-relaxing, anticonvulsive or anxiolytic effect.

30. The method of claim 29, wherein the daily dosage is 0.002 to 1.0 mg./kg. of body weight.

31. A pharmaceutical composition of claim 28 adapted for oral administration.

32. A pharmaceutical composition of claim 31 in tablet, dragee or capsule form.

33. A pharmaceutical composition of claim 31 wherein the unit dosage amount is between 1 and 20 mg.

34. A method according to claim 29 wherein the administration is oral.

35. A compound of the formula:

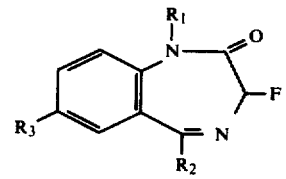

wherein $R_1$ is hydrogen or alkyl having 1 to 4 carbon atoms;
$R_2$ is phenyl, monohalophenyl or pyridyl;
$R_3$ is F, Cl, Br or $NO_2$,
and pharmaceutically acceptable acid addition salts thereof.

36. A muscle-relaxing, anti-convulsive and anxiolytic composition which comprises an amount effective for the aforesaid uses of a compound of claim 35 in admixture with a pharmaceutically acceptable carrier.

37. A method for producing muscle relaxation in mammals which comprises administering an effective skeletal muscle relaxant amount of a compound of claim 35 to the mammal.

38. A method for relieving anxiety in mammals which comprises administering an effective anxiolytic amount of a compound of claim 35 to the mammal.

39. A compound of the formula

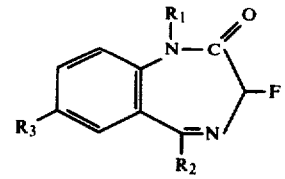

wherein $R_1$ is hydrogen, alkyl having 1 to 4 carbon atoms or $-CH_2CF_3$; $R_2$ is phenyl, monohalophenyl or pyridyl; $R_3$ is F, Cl, Br or $NO_2$, and the pharmaceutically acceptable acid addition salts thereof.

* * * * *